(12) United States Patent (10) Patent No.: US 8,748,816 B2
Kooijman et al. (45) Date of Patent: Jun. 10, 2014

(54) CLUSTERING OF MULTI-MODAL DATA

(75) Inventors: Cornelis Sander Kooijman, Veldhoven (NL); Sander Richard Marie Stoks, Nijmegen (NL)

(73) Assignee: FEI Company, Hillsboro, OR (US)

( * ) Notice: Subject to any disclaimer, the term of this patent is extended or adjusted under 35 U.S.C. 154(b) by 12 days.

(21) Appl. No.: 13/546,863

(22) Filed: Jul. 11, 2012

(65) Prior Publication Data

US 2013/0015351 A1 Jan. 17, 2013

Related U.S. Application Data

(60) Provisional application No. 61/506,441, filed on Jul. 11, 2011, provisional application No. 61/570,603, filed on Dec. 14, 2011.

(30) Foreign Application Priority Data

Dec. 14, 2011 (EP) .................................... 11193495

(51) Int. Cl.
*H01J 37/28* (2006.01)
*H01J 37/244* (2006.01)

(52) U.S. Cl.
USPC ............ 250/310; 250/305; 250/306; 250/307

(58) Field of Classification Search
USPC .................................. 250/305, 306, 307, 310
See application file for complete search history.

(56) References Cited

U.S. PATENT DOCUMENTS

| | | | |
|---|---|---|---|
| 6,584,413 B1 * | 6/2003 | Keenan et al. ................... 702/28 |
| 7,130,374 B1 * | 10/2006 | Jacobs et al. ..................... 378/76 |
| 7,490,009 B2 | 2/2009 | Gottlieb et al. | |
| 7,979,217 B2 | 7/2011 | Gottlieb et al. | |
| 8,080,791 B2 * | 12/2011 | von Harrach et al. ......... 250/311 |
| 8,093,556 B2 * | 1/2012 | Zeile ............................. 250/306 |
| 8,222,598 B2 * | 7/2012 | Statham et al. ................ 250/306 |
| 8,232,523 B2 * | 7/2012 | Boughorbel et al. .......... 250/307 |
| 8,334,511 B2 * | 12/2012 | Schamber et al. ............. 250/311 |
| 8,450,215 B2 * | 5/2013 | Mantz et al. ................... 438/706 |
| 2010/0059672 A1 * | 3/2010 | Zeile ............................. 250/282 |
| 2010/0148064 A1 * | 6/2010 | Harrach et al. ................ 250/307 |
| 2011/0144922 A1 | 6/2011 | Corbett et al. | |
| 2011/0301869 A1 | 12/2011 | Gottlieb et al. | |
| 2013/0015351 A1 * | 1/2013 | Kooijman et al. ............. 250/307 |
| 2013/0037714 A1 * | 2/2013 | Boughorbel et al. .......... 250/307 |
| 2013/0037715 A1 * | 2/2013 | Boughorbel et al. .......... 250/307 |
| 2013/0126728 A1 * | 5/2013 | Waiblinger et al. ........... 250/305 |

* cited by examiner

*Primary Examiner* — David A Vanore
(74) *Attorney, Agent, or Firm* — Scheinberg & Associates, PC; Michael O. Scheinberg; John B. Kelly

(57) ABSTRACT

Information from multiple detectors acquiring different types of information is combined to determine one or more properties of a sample more efficiently than the properties could be determined using a single type of information from a single type of detector. In some embodiments, information is collected simultaneously from the different detectors which can greatly reduce data acquisition time. In some embodiments, information from different points on the sample are grouped based on information from one type of detector and information from the second type of detector related to these points is combined, for example, to create a single spectrum from a second detector of a region of common composition as determined by the first detector. In some embodiments, the data collection is adaptive, that is, the data is analyzed during collection to determine whether sufficient data has been collected to determine a desired property with the desired confidence.

20 Claims, 11 Drawing Sheets

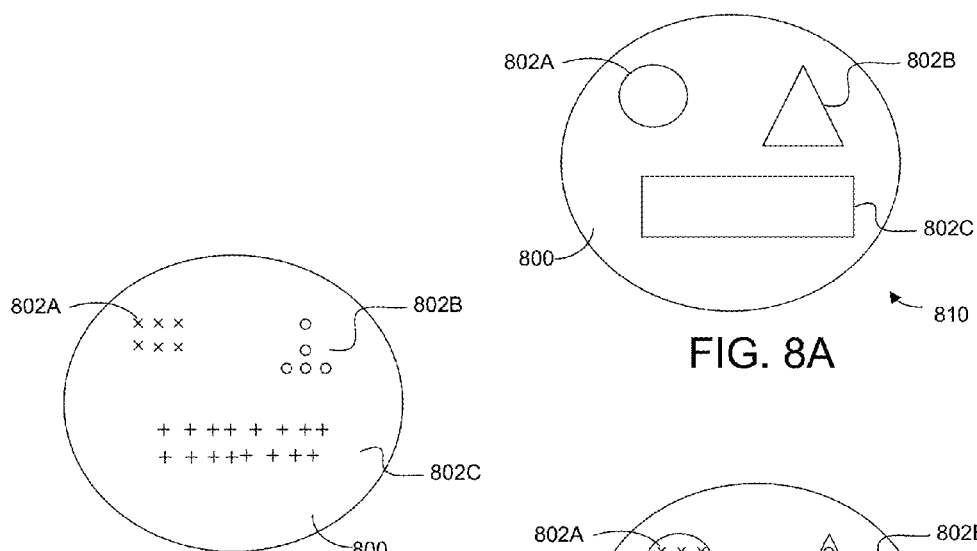
FIG. 8A
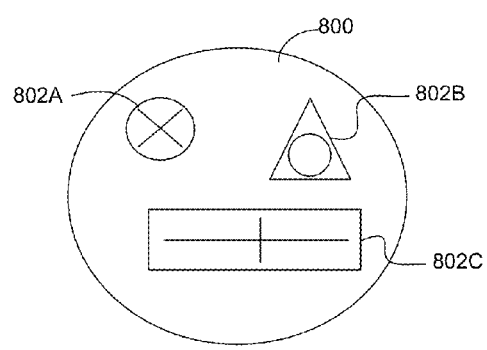
FIG. 8B
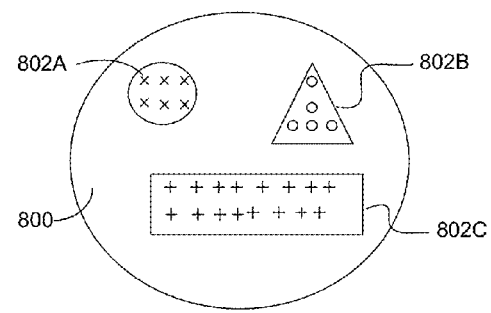
FIG. 8C
FIG. 8D

CLUSTERING OF MULTI-MODAL DATA

This application claims priority from U.S. Provisional Patent Application 61/479,190, filed Jul. 11, 2011, and U.S. Provisional Patent Application 61/570,603, filed Apr. 26, 2011, which are hereby incorporated by reference.

TECHNICAL FIELD OF THE INVENTION

The present invention relates combining data acquired by different analytical modes to determine characteristics of a sample.

BACKGROUND OF THE INVENTION

Mineral analysis systems, such as the Qemscan and MLA available from FEI Company, Hillsboro, Oreg., have been used for many years to analyze mineral samples. To determine the type and relative quantity of minerals present in a mine, a sample in the form of small granules, is fixed in epoxy in a mold and the mold is placed in a vacuum chamber. An electron beam is directed toward a sample and, in a process called "energy dispersive x-ray spectroscopy" or "EDS," the energies of x-rays coming from the sample in response to the electron beam are measured and plotted in a histogram to form a spectrum. The measured spectrum can be compared to the known spectra of various elements to determine which elements and minerals are present. FIG. 1 shows a typical sample 100 having granules 102 embedded in epoxy matrix 104.

It takes considerable time to accumulate an x-ray spectrum. When an electron in the primary beam impacts the sample, the electron loses energy by a variety of mechanisms. One energy loss mechanism includes transferring the electron energy to an inner shell electron, which can be ejected from the atom as a result. An outer shell electron will then fall into the inner shell, and a characteristic x-ray may be emitted. The energy of the characteristic x-ray is determined by the difference in energies between the inner shell and the outer shell. Because the energies of the shells are characteristic of the element, the energy of the x-ray is also characteristic of the material from which it is emitted. When the number of x-rays at different energies is plotted on a graph, one obtains a characteristic spectrum, such as the spectrum of pyrite shown in FIG. 2. The peaks are named for the corresponding original and final shell of the electron that originated the x-ray. FIG. 2 shows the sulfur $K\alpha$ peak, the iron $K\alpha$ peak and the iron $K\beta$ peaks.

Many primary electrons must strike the sample to produce sufficient x-rays to create an identifiable spectrum. Not every incoming electron will knock out an inner shell electron, and different inner shell electrons may be ejected, with the gap being filled by different outer shell electrons. Because the x-ray detector subtends a relatively small solid angle, only a relatively small number of the emitted x-rays are detected. The probability of an incoming electron causing the emission of a detectable x-ray of a particular energy depends on many factors, including the elemental composition of the sample, the energy of the incoming electron, the geometric relation between the electron beam, the sample surface, and the detector, the likelihood of a particular inner shell electron absorbing the energy of a primary beam electron, and the likelihood of a particular outer shell electron angle dropping to the vacancy in the inner shell.

Moreover, the energy measurement of the electron, like any measurement, has an inherent error. Thus, rather than a spectrum showing a peak corresponding to an electron transition at a single value, the peak will be spread over a range of values. Because the peaks from different transitions of different elements can overlap, a large number of x-rays is collected to more precisely define the locations of the peak. Several million x-rays, each referred to as a "quant," are typically detected to form a reliable spectrum in which the most important peaks can be identified with sufficient confidence. U.S. Pat. Publication No. 2011/0144922, which is assigned to the assignee of the present application, describes an algorithm that allows elements to be determined with reasonable confidence using a smaller number of detected x-rays, for example, a thousand x-rays.

Other emissions besides characteristic x-rays are detectable when an electron beam impacts a sample surface. Background, or Bremsstrahlung, radiation comprise x-rays spread over a wide range of frequencies and can obscure characteristic x-ray peaks. Secondary electrons, Auger electrons, elastically and inelastically forward or backward scattered electrons, and light can be emitted from the surface upon impact of a primary electron beam and can be used to form an image of the surface or to determine other properties of the surface. Backscattered electrons are typically detected by a solid state detector in which each backscattered electron is amplified as it creates many electron-hole pairs in a semiconductor detector. The backscattered electron detector signal is used to form an image as the beam is scanned, with the brightness of each image point determined by the number of backscattered electrons detected at the corresponding point on the sample as the primary beam moves across the sample.

Backscattering of electrons depends on the atomic number of the elements in the surface and upon the geometric relationship between the surface, the primary beam, and the detector. The backscattered electron image therefore shows contour information, that is, boundaries between regions of different composition, and topographical information. Obtaining a backscattered electron image requires collecting only a sufficient number of electrons at each point to produce a reasonable contrast between points having different properties and so is much faster than obtaining a sufficient number of x-rays to compile a complete spectrum at each point. Also, the probability of an electron being backscattered is greater than the probability of the electron causing the emission of a characteristic x-ray of a particular frequency. Obtaining sufficient backscattered electron image data at a single dwell point typically takes less than a microsecond, whereas acquiring sufficient x-rays to obtain an analyzable spectrum at a single dwell point typically takes more than a millisecond.

In one mode of operating the MLA system, an image is first acquired using a backscattered electron detector, and the image is then processed to identify regions that appear from the contrast to have the same elemental composition. The beam is then positioned at the centroid of each identified region for a longer dwell time to collect an x-ray spectrum representative of the region. X-rays generated during the backscattered electron detector scan are not used.

While some systems include a "fast mapping" mode to produce a "spectrum cube," that is, a two-dimensional map of a sample, with the composition of the material at each point providing the third dimension of the cube, the "fast map" still requires sufficient time at each dwell point to collect enough x-rays to determine the type and quantity of elements present at the pixel.

SUMMARY OF THE INVENTION

An object of the invention is to provide a method and apparatus for more rapidly acquiring information about a sample.

A method entails forming a first image using a first modality, forming a second image using a second modality, and combining information from the first image and from the second image to form a third image. In a preferred embodiment, information from the first image is compositional information of the sample and the information from the second image is topographical and/or contour information. In some embodiments, the first image and the second image are made by scanning a beam of photons or a beam of charged particles across a sample. The first image and the second image can be acquired simultaneously or sequentially. The integration time for the detectors used in the two modalities may be the same or may be different. In some embodiments, the superior resolution of one modality is used to enhance the resolution of the other modality. In some embodiments, the faster acquisition rate of one modality is used to group and to combine information from the other modality to provide information more rapidly. In some embodiments, information from one modality is used to enhance the analysis of the second modality.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 8 illustrates the steps of FIG. 7.

DETAILED DESCRIPTION OF PREFERRED EMBODIMENTS

Figure 1:
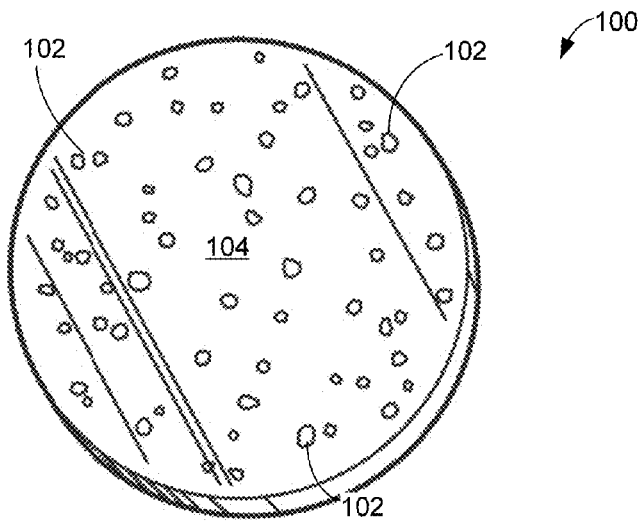
FIG. 1 is a typical sample plug for viewing in an EDS analysis system.
Figure 2:
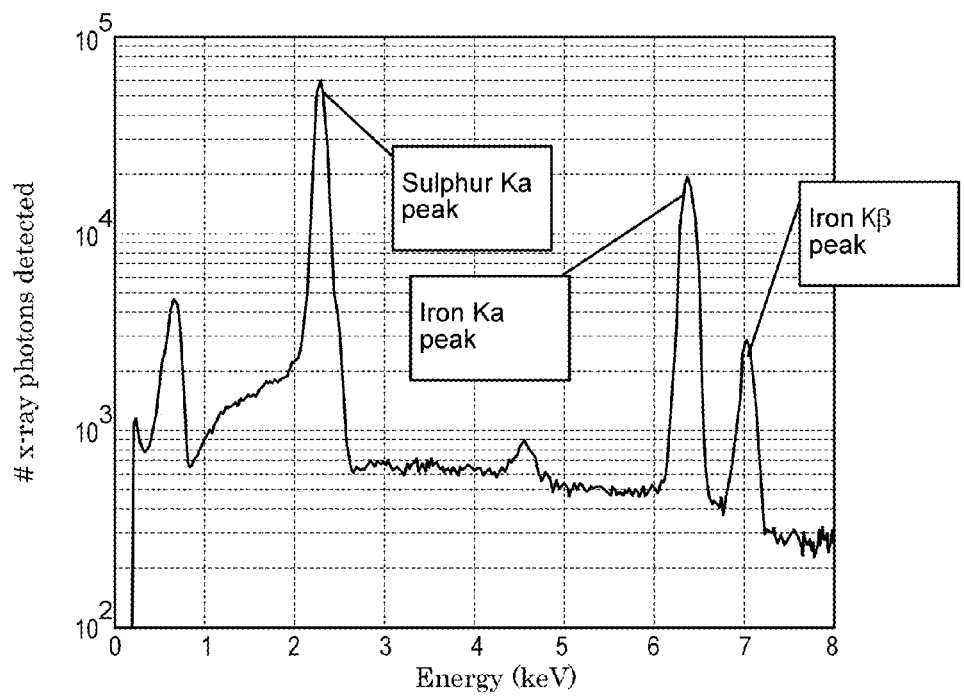
FIG. 2 shows an x-ray spectrum of pyrite, which includes iron and sulfur.

In accordance with a preferred embodiment of the invention, data is combined from different analysis modalities to determine properties of a sample. A beam is typically directed toward a sample surface and emissions generated from the surface by the beam impact are detected. The primary beam can comprise, for example, electrons, ions, photons (e.g., a laser beam or x-rays), or atoms. The beam is typically focused to a point on the sample and the point is scanned across the sample. In some modalities, the beam may be parallel instead of focused and/or stationary instead of being scanned.

Particles (used herein to include photons and scattered primary particles) that are emitted, backscattered, or transmitted through the sample in response to the primary beam are detected. Different emissions from the sample, such as x-rays, backscattered electrons, secondary electrons, Auger electrons, transmitted electrons, or photons, are detected in various analysis modalities. The invention is not limited to any particular analytical technique.

The different modalities may provide different information about properties of the sample, such as contour information, compositional information, topographical information, or chemical state information.

In some embodiments, different detectors detect different types of emissions generated at the same time by a beam, to provide synchronized, simultaneous acquisition of multimodal data. For example, backscattered electron data may be acquired at the same time as x-ray data, with the x-rays being placed at the correct location in the backscattered electron image to produce a spectrum cube. In some embodiments, the different analysis modalities include detecting emissions generated by different beams at different times.

The different modalities may have different acquisition rates or different resolutions. Information from one technique, typically the more sensitive modality or the higher resolution modality, is used to supplement information from another modality, thereby decreasing the acquisition time or increasing the resolution of the other techniques. For example, some embodiments analyze the data from a more sensitive detector and use the data to group dwell points to combine/average/integrate the scarce information of the less sensitive detector. A backscattered electron detector image can be used to find regions on the sample that have similar appearances in the image and that are therefore likely to have similar properties. For example, regions that have the same appearance may include the same phase or element. The x-ray spectra from similar appearing regions can be combined to produce a combined spectrum that will include many more quanta than the individual spectrum from a pixel. These high quality spectra can then be analyzed to determine the type and relative quantities of materials present in the sample. By combining spectra from multiple points, the need to re-visit particle/phase locations may be eliminated in some cases, so the process can continue on to image a different part of the sample while the previous data cube is being processed.

Some embodiments of the invention allow a spectrum cube to be acquired more efficiently than in the prior art. An electron beam is directed toward a sample and scanned across regions having different characteristics, such as different mineral compositions. A first detector may provide information about contour or topography, for example, by detecting backscattered electrons, while a second detector provides information about composition, for example, by detecting characteristic x-rays. A 1k×1k backscattered electron detector image can be acquired much faster than a full spectrum cube can be filled with discernible spectra at each pixel location. The difference in image acquisition time can be orders of magnitude. For example, a backscattered electron intensity value for an individual dwell point can be acquired in about 1 microsecond, wherein obtaining sufficient x-ray quants for an individual dwell point can take 1 or 10 milliseconds. For an image of 1k×1k pixels, backscattered electron data to determine a contour can therefore be acquired in about one second, whereas obtaining the compositional information from the x-ray detector can take from about fifteen minutes to a few hours. Thus, the x-ray data is about $10^4$ times more sparse than the data from the backscattered electron detector. For a three-dimensional image, the times required to obtain the images are correspondingly larger. For example, creating a tomogram using a tilt series of between −70 degrees and positive 70 degrees, with one degree increments, would take about 140 times longer than obtaining a single two-dimensional image. The benefits of the invention are correspondingly greater for three-dimensional imaging.

In some embodiments, different detectors can integrate their respective signals over different time periods and different points on the sample surface. For example, a first detector, such as a backscattered electron detector, can collect a signal while the beam is positioned at an individual dwell. The detector integrates the signal collected during the dwell period. When the beam is ready to move to the next dwell point, the integrated signal value from the first detector is stored, the integrator is reset, and the integration begins anew at the next dwell point. A second detector, such as an x-ray detector, can continue to integrate the x-ray signal as the beam is moved to the next dwell point and integrates its signal over a group of multiple dwell points. Thus, the integration period for the two detectors is different, even though the different signals coming from the sample are being generated by the same beam. In such embodiments, the region from which the signal is generated is different for the two detectors—the region from which the signal is generated for the detector with the shorter integration time is typically a subset of the region from which the signal is generated for the detector with the longer integration time.

Additional modalities can be used to determine regions of the same chemical content or can be used to enhance the confidence that dwell points belong to regions with the same chemical content. For example, cathodeluminescence, the emission of photons of a characteristic frequency upon bombardment of the sample with an electron beam, can be used to determine regions having similar composition, either alone or to enhance the backscattered electron data. Information about the sample can also be inferred from known compositional information of the sample. For example, if two elements form a compound and one is more easily detected by x-ray analysis, the extent of the region of the less detectable element can be assumed to be coextensive with the element with which it forms a compound.

In some embodiments, the process is adaptive, that is, the data acquisition is adjusted as the data is being acquired, to determine whether sufficient data has been acquired for the analysis. For example, in a fast mapping situation where the beam is scanning rapidly, the system can repeatedly scan a region until it is determined that sufficient information has been detected. For example, elements having overlapping peaks typically require more quants to differentiate from each other than elements having more unique x-ray peaks. If the analysis shows an easily identifiable element, the system may collect fewer quants. If the analysis shows an element having a peak known to overlap the peak of another element, the region can be scanned multiple times to collect additional x-rays to provide an enhanced signal-to-noise ratio to differentiate the peak. Thus, some embodiments adjust the amount of data collected based on analysis of the data as it is being collected. As additional x-rays are collected, additional backscattered electrons may also be collected and used to refine the boundary of the region. The x-ray information can also be used to refine the shape by differentiating regions that appear similar in the backscattered electron image but have different compositions.

A set of data mapped to points of the sample is referred to as an "image." An "image" is not limited to displaying the visual appearance of the sample and is not limited to information displayed in an observable manner. For example, a data table stored in a computer and having composition or chemical state for points on the sample is an "image," as is a picture of the sample on a display screen. Data sets representing three-dimensional maps are also included in the definition of "image."

Figure 3:
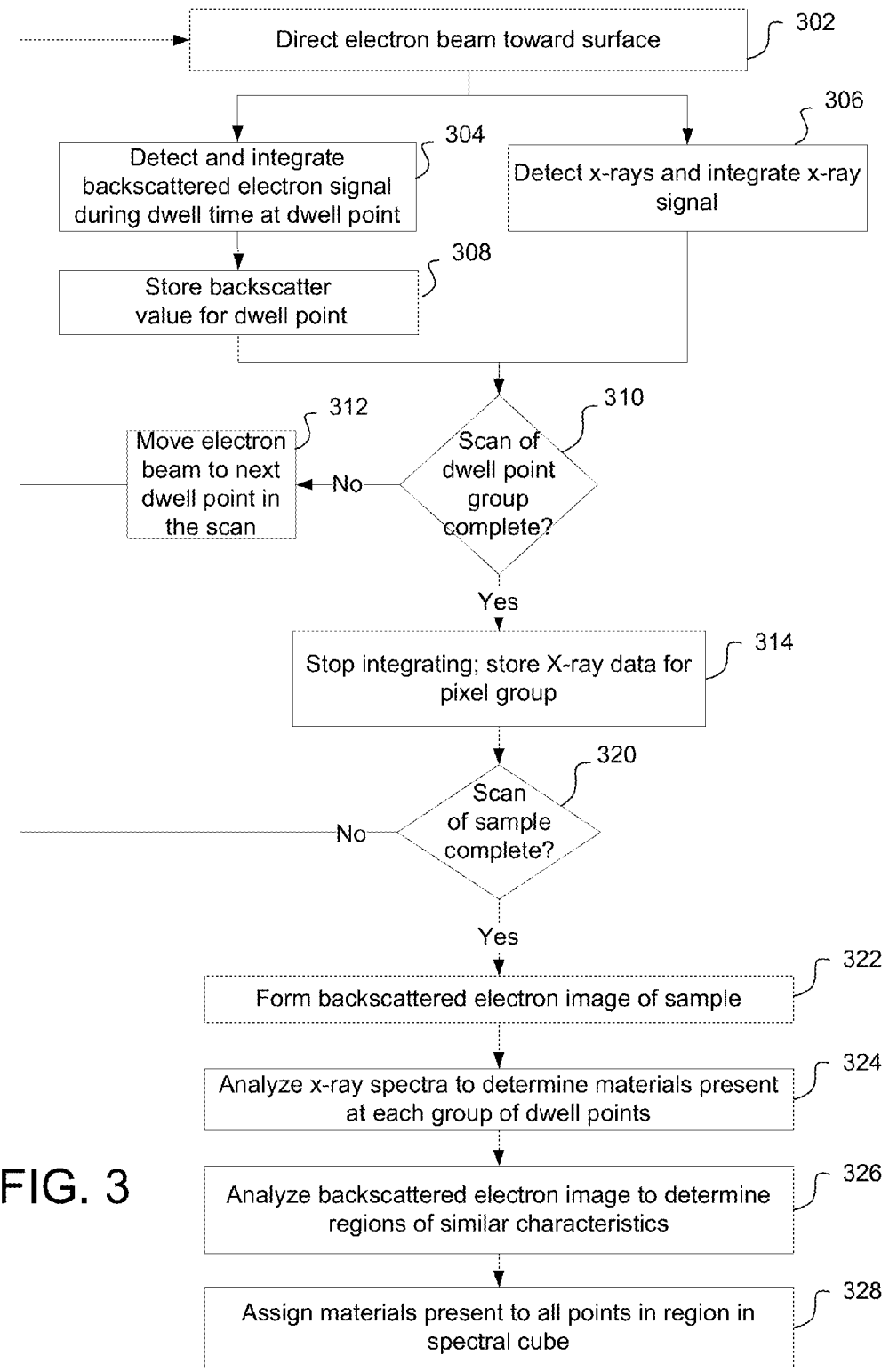
FIG. 3 is a flow chart of a method in which data from two modalities having different integration rates are combined.
Figure 4:
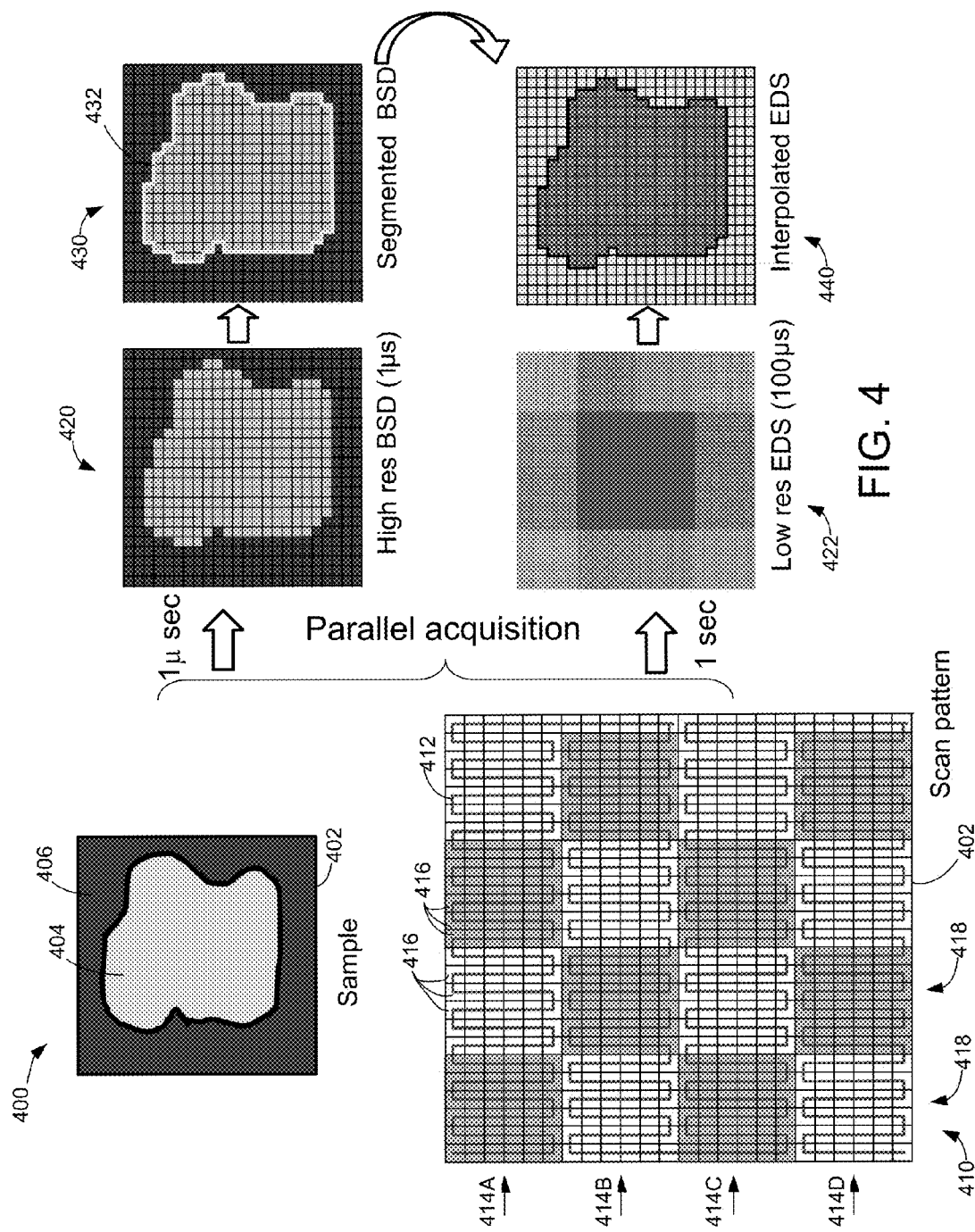
FIG. 4 illustrates the steps of FIG. 3.

FIG. 3 shows the steps of a method of the invention. FIG. 4 illustrates the steps of FIG. 3. Image 400 depicts a sample 402 comprising a portion of a mold such as that shown in FIG. 1 and having a relatively homogeneous region 404 surrounded by epoxy 406. In step 302, a focused electron beam is directed toward a dwell point on the sample surface. The electron beam is typically focused to a spot size of less than a micron and preferably less than 100 nm.

Figure 12:
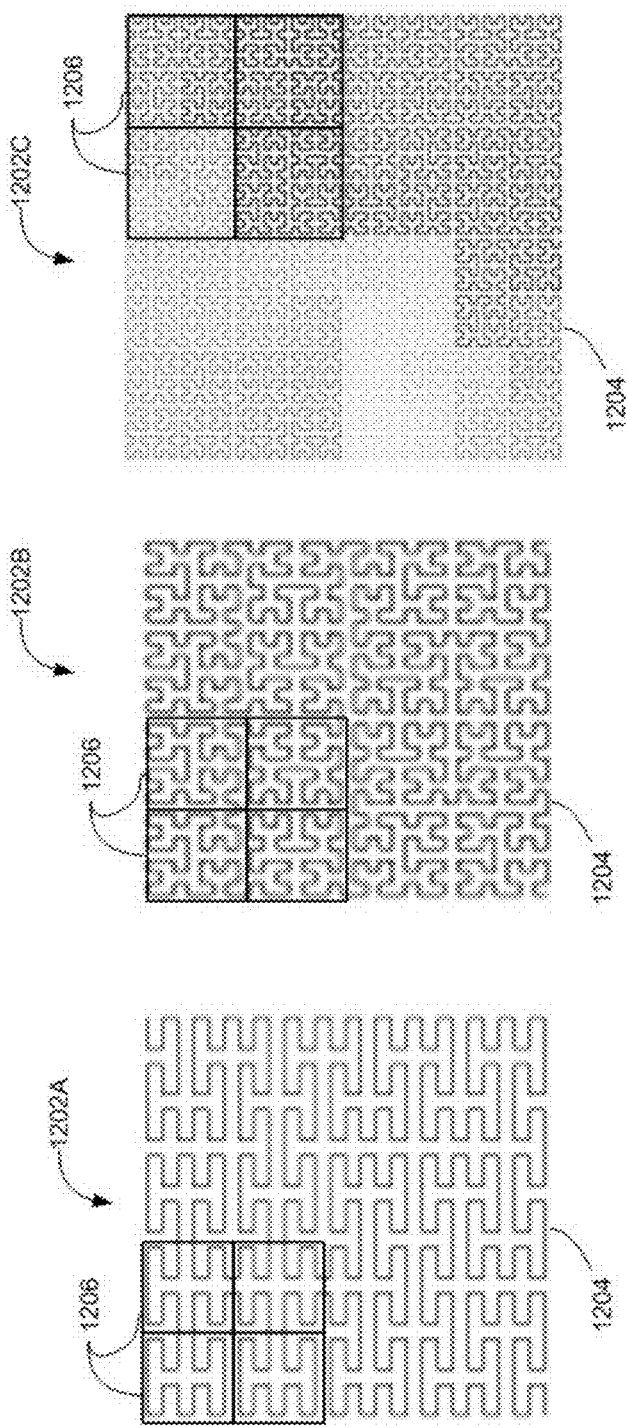
FIG. 12 shows example scan patterns that can be used with some embodiments of the present invention.

Image 410 shows an example scan pattern 412 on the sample 402. The scan pattern shows the sequence of dwell points to which the beam is directed. Scan pattern 412 is a second order serpentine pattern, which has a large serpentine pattern that moves back and forth along the four large rows 414A-414D, and a smaller serpentine pattern up and down within each of large row 414A-414D. That is, the smaller serpentine pattern is nested within the larger serpentine pattern. The grid of horizontal and vertical lines shows the individual dwell points 416. Backscattered electron information is integrated and stored for each dwell point. The alternating light and dark regions show the dwell point groups 418 over which the x-ray data is integrated. Other types of scan patterns, such as scan patterns defined by continuous fractal space- or plane-filling curves such as Hilbert or Moore curves, can be used. FIG. 12 shows examples of Hilbert curves 1202A and 1202B, and an example of a Moore curve 1202C. Lines 1204 show the scan lines, with data for individual pixels from the faster detector, such as a backscattered electron detector, being integrated at individual dwell points along scan lines 1204. Data for individual pixels from the slower detector being integrated within boxes 1206 that include multiple dwell points. Scan patterns are not limited to two-dimensional patterns.

Multiple detectors could be used with different integration times, with the fastest detector (that is, the detector with the shortest integration time) integrating at the lowest level of the fractal or other pattern and providing the highest resolution, with successively slower detectors integrating at successively higher levels of the pattern and providing successively lower resolution. That is, differently sized groups of dwell points corresponding to different scale factors provide different integration times.

In step 304, backscattered electrons emitted from the surface are detected by a backscattered electron detector, which integrates the signal detected while the beam is positioned at a dwell point. Before the beam moves to the next dwell point in the scan, the integrated backscattered electron signal from the current dwell point is stored in step 308. In step 306, x-rays emitted from the surface in response to the primary electrons are detected and their energies measured by a spectrometer, such as an energy dispersive x-ray spectrometer. The backscattered electrons and the x-rays are preferably detected simultaneously. The x-ray signal is also integrated while the beam is positioned at the dwell point. In a preferred embodiment, however, the x-ray signal continues to be integrated over a group of several dwell points. The integration is not completed, and a value is not stored, at the end of every dwell point.

If in decision block 310, it is determined that the beam has not scanned all the dwell points in a group of dwell points for integrating the x-ray signal, then integration continues for the x-ray detector and the electron beam is directed in step 312 to the next dwell point in the scan. If in decision block 310, it is determined that the beam has scanned all the dwell points in a group of dwell points for integrating the x-ray signal, then in step 314 the integration is stopped and the integrated x-ray information for the pixel group is stored.

If it is determined in decision block 320 that the scan of the sample is not complete, that is, not all dwell point groups in the sample have been scanned, then the electron beam is directed to the first dwell point in the next dwell point group in step 302, and the data collection process continues, with backscattered electron information from each dwell point being stored and x-ray information from each group of dwell points being stored.

If it is determined in decision block 320 that the scan is complete, the backscattered electron data are used to form an image 420 of the sample in step 322. The brightness of each pixel in the image 420 is determined by the number of backscattered electrons integrated at each dwell point 416. In step 324, the x-ray data spectrum integrated over each group 418 of dwell points is analyzed to determine a composition for each group 418 of dwell points. As can be seen by comparing images 420 and 422, each pixel of the x-ray image corresponds to multiple pixels in the backscattered electron image because the requirement to have many more x-rays to form an analyzable spectrum necessitates integrating over a larger region. In step 324, the x-ray spectrum of each group of dwell points that correspond to a pixel is analyzed to determine the elements present at the dwell point.

In step 326, the backscattered electron image is analyzed to determine the outline of regions of the sample having similar characteristics. Image 430 shows a border 432 drawn around a region that shares a common gray level in the backscattered electron detector image and is assumed to be composed of the same material. In step 324, the regions of common gray level in the backscattered electron image are correlated with the larger pixels in the x-ray image 422, and the corresponding pixels in the backscattered electron map are assigned the materials determined by the spectrum of the corresponding pixels in the x-ray map. Image 440 shows an interpolated compositional map of the sample, which was determined by assuming that regions having similar backscattered electron image characteristics are composed of the same material, which is determined by the x-ray map.

FIGS. 3 and 4 show how the lower resolution of one technique can be improved by the higher resolution of a second technique. In the method of FIGS. 3 and 4, the higher resolution of one type of detector, the backscattered electron detector, is thus "transferred" to the other type of detector, the x-ray detector, to provide the compositional information from the first, low resolution detector, the EDS detector, at the higher resolution of the second detector, the backscattered electron detector. In the method of FIGS. 3 and 4, information is acquired by multiple detectors simultaneously, one detector providing contour information and one providing compositional information, although the integration time of the two detectors differed. In other embodiments, the information could be acquired sequentially and/or the integration time could be the same for both detectors. Optionally, by combining the x-rays from all regions within particle 402, sufficient x-rays may be collected to produce a spectrum more rapidly or a spectrum that can be analyzed with higher confidence. Combining the x-rays detected from dwell points determined by the backscattered electron analysis to have the same materials greatly decreases the time required to acquire sufficient x-rays to determine the composition. While exemplified by a primary electron beam, a backscattered electron detector, and an x-ray detector, the invention is not limited to any particular primary beam or any particular type secondary particle or energy detection.

The spatial resolution of some analysis techniques depends in part on the interaction volume between the primary beam and the sample, that is, on the volume from which detectable particles are emitted when impacted by a primary beam. This interaction volume depends on the size and energy of the primary beam, the path of the particles in the primary beam within the sample as they are scattered and gradually lose energy, and the ability of the particles being detected to emerge from within the sample. One can determine statistically how deep and how wide the path of a typical primary electron will be and the likelihood that a backscattered electron or x-ray will emerge from the sample from a particular depth. For example, secondary electrons and Auger electrons do not have sufficient energy to emerge from deep within the sample, and so have smaller interaction volumes compared to backscattered electrons or characteristic x-rays.

Figure 5:
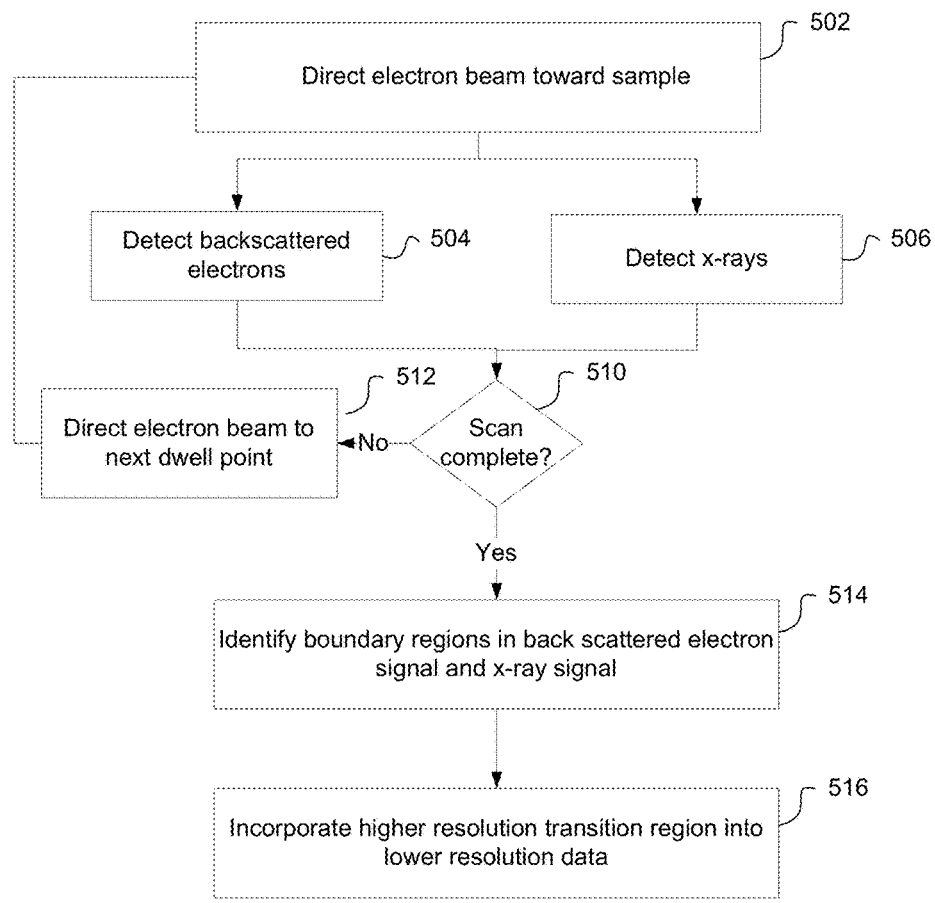
FIG. 5 is a flow chart of a method that combines data from two modalities having different resolutions to improve the resolution of an image formed from the lower resolution modality.

FIG. 5 is a flowchart illustrating another aspect of the invention. FIGS. 6A-6E illustrate the method of FIG. 5. In the method shown in FIGS. 5 and FIGS. 6A-6E, information from a higher resolution detector is used to "sharpen up" or improve the resolution of a lower resolution detector. In the embodiment described, information from a higher resolution detector that provides contour information is used to improve the resolution of a detector that provides compositional information. In this embodiment, the detectors can measure the sample simultaneously or sequentially, Simultaneous measurement reduces the need for exact image registration methods. The integration time of the detectors may be the same or different, that is, the detectors may acquire information over the time periods of the same duration, or the detectors may acquire information during time periods of different durations. The resolutions of the detectors are different, for example, because the interaction volumes of the beam for the detected particles from the different detectors are different, or because the detectors use stimulating beams of different sizes. In some embodiments, as a beam scans a phase interface or boundary at which the same properties change, the higher resolution modality will more accurately locate the boundary. The more accurately located boundary of the higher resolution modality can be incorporated into the image from the lower resolution modality to locate the change in property measured by the lower resolution modality more accurately.

Figure 6A:
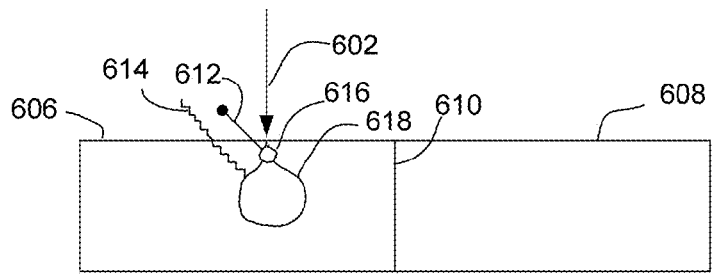
FIG. 6 illustrates the steps of FIG. 5.
Figure 6B:
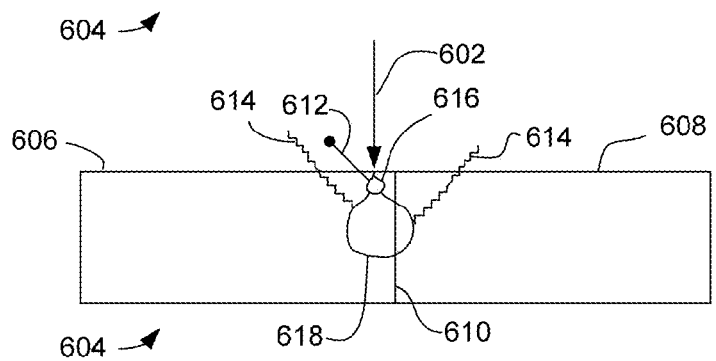

In step 502, an electron beam 602 is directed toward a sample 604 comprised of two materials, a first material 606 and a second material 608 separated by an interface or boundary 610. Electron beam 602 causes the emission of backscattered electrons 612 and x-rays 614 at each dwell point. Backscattered electrons come primarily from the interaction volume 616, while x-rays are emitted from the larger interaction volume 618. Interaction volume 618 for x-rays is larger than interaction volume 616 because backscattered electrons generated deep in the sample have a lower probability of emerging from the surface than do x-rays generated at the same depth as the x-rays interact less strongly with the sample material. FIG. 6B shows that as the beam 602 approaches the boundary 610, the smaller interaction volume 616 of the higher resolution modality is entirely within material 606, whereas the larger interaction volume of the lower resolution modality exists within material 606 and material 608, resulting in a signal having characteristics of both.

In step 504, backscattered electrons are detected by a backscattered electron detector and in step 506, x-rays are detected by an x-ray detector, such as one or more silicon drift detectors, that measures the energy of the x-rays emitted in response to the impact of the primary beam. If decision block 510 determines that the scan is not complete, the primary electron beam is scanned in step 512 to the next dwell point, and additional x-rays and backscattered electrons are collected. As shown in FIG. 6B, when the electron beam 602 impinges on sample 604 away from a boundary 610, the backscattered electron and the x-ray signal will both be representative of only material 606. As the beam 602 approaches boundary 610, the interaction volumes will contain material from both sides of the boundary 610, blurring the signal.

Figure 6C:
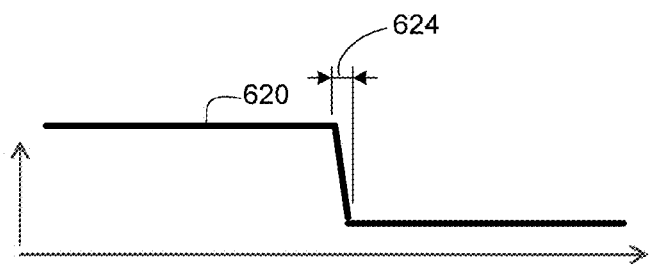

FIG. 6C shows a signal 620 from a backscattered electron detector. The first material 606 backscatters more electrons than second material 608. As the primary beam 602 moves toward the boundary 610, the strength of the backscattered electron signal changes over region 624 from being representative entirely of first material 606 to being representative entirely of second material 608. Region 624 is typically equal to the width of interaction volume 616.

Because the interaction volume 616 of the backscattered electron is relatively small, the boundary is relatively sharp and its location can be determined at relatively high resolution.

Figure 6D:
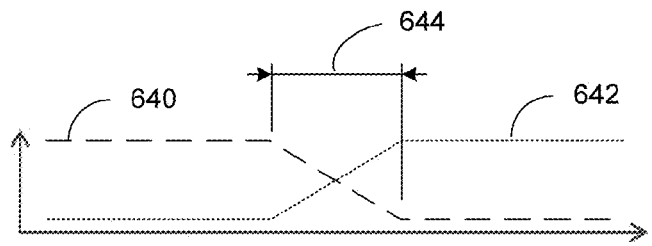

FIG. 6D shows an x-ray signal 640 representative of a first x-ray energy characteristic of the first material 606 and an x-ray signal 642 of a second x-ray energy characteristic of the second material 608. As the electron beam moves across the region of material 606, signal 640 corresponding to the first material shows a constant magnitude and a signal 642 is in the level of noise for Bremsstrahlung radiation. As the electron beam 602 approaches boundary 610, the x-ray signal 640 representative of material 606 begins to decrease toward a noise level, while the x-ray signal 642 representative of material 608 begins to increase from a noise level to a significant signal. The width 644 of the region in which both signals are present is approximately equal to the width of the interaction volume for x-ray emission. As is clear from comparing FIGS. 6D and FIG. 6C, because the interaction volume of the x-ray signal is larger than the interaction volume of the backscattered electron signal, width 644 is greater than width 624, thereby providing a lower positional resolution for the compositional x-ray data.

Figure 6E:
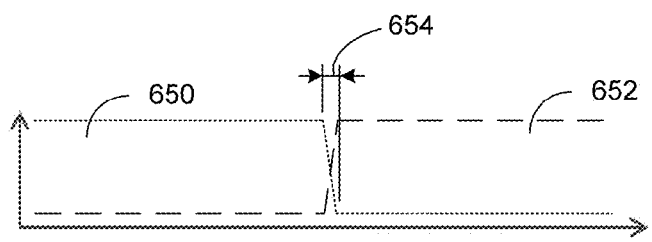

In step 514, the boundary layer is identified in both analysis modalities, that is, in the backscattered electron signal 620 and in the x-ray signals 640 and 642. In step 516, the boundary layer width of the higher positional resolution backscattered electron signal is applied to the transition region of the lower resolution signal, the x-ray signal. FIG. 6E shows modified compositional x-ray data 650 representative of the first material 606 and modified compositional x-ray data 652 representative of the second material 608. The x-ray compositional data is modified by combining it with the higher resolution of the transition region backscattered electron data, to provide a transition region 654 of the x-ray data that has the length of the transition region 624 of the backscattered electron signal. The combined signal shows the composition of the sample with the greater positional resolution of the backscattered electron detector. If the boundary 610 is not sharp, that is, if the composition changes gradually over a length, then the backscattered electron image will also show a gradual change in the image, and the x-ray image.

When using one modality to sharpen up the information from a second sensor the deconvolution of the image is preferably performed using a technique, such as principal component analysis. The sharpening of the first image is preferably based on a deconvolution technique in which the deconvolution kernel is derived from the second image. Because images that are acquired simultaneously are already perfectly aligned, the position of the edges is known.

Figure 7:
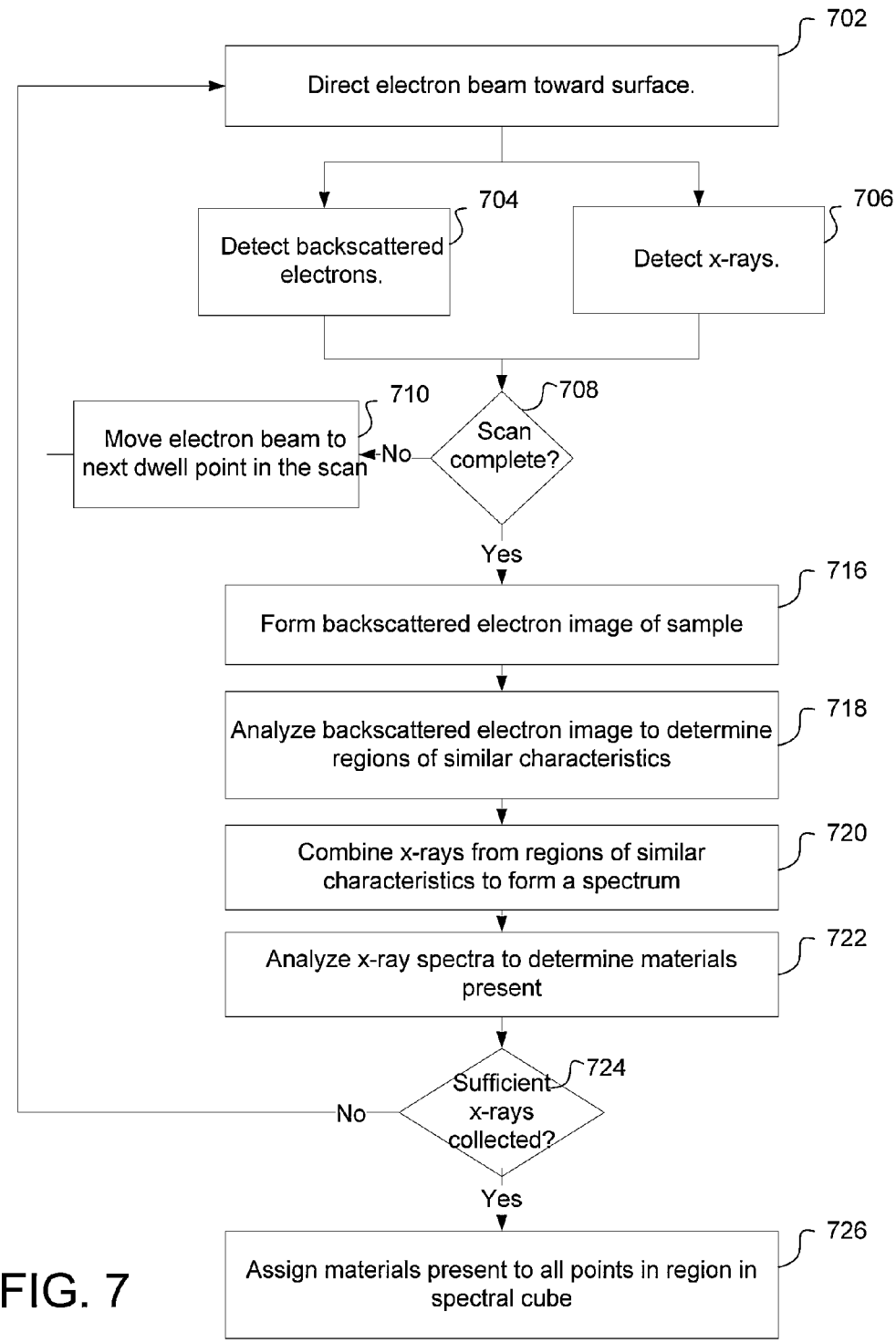
FIG. 7 is a flow chart of a method that use properties of a first type of measurement to improve the results of a second type of measurement.

FIG. 7 describes another aspect process of the invention, as illustrated by FIGS. 8A-8D. FIGS. 7 and 8A-8D show a system in which the images are acquired using two analysis modalities, a first modality that acquires information rapidly and a second modality that acquires information more slowly. The first modality is used to determine points having a common property, and then information from the second modality from those points is combined to form a third image. The second modality, which requires a long integration time to characterize an individual point, does not then need to dwell at each point for sufficient time to characterize that point—the characterization information is accumulated from multiple points as grouped by the first modality. The beam can therefore scan at a rate that is compatible with the first modality, and does not need to slow down to collect enough information from each dwell point for the second modality.

For example, a first detector, such as a backscattered electron detector or a secondary electron detector, can determine contours of regions of similar appearance during a rapid scan, while the second detector simultaneously (or sequentially) collects compositional information, such as x-ray quants, from each dwell point. The compositional information from all dwell points within each contour are combined to determine the composition within the contour for a third image. The electron beam scan may provide a sufficient dwell time to form a backscattered electron image or a secondary electron image, but insufficient dwell time to collect sufficient x-ray quants to determine the composition for individual dwell points.

FIG. 8A shows a sample 800 typically comprising a portion of a plug such as that shown in FIG. 1, containing three distinct regions, 802A, 802B, and 802C. In step 702, an electron beam is directed toward the surface of sample 800, which comprises bits of material in an epoxy matrix. In step 704, backscattered electrons emitted from the surface are detected by a backscattered electron detector. In step 706, x-rays emitted from the surface in response to the primary electrons are detected and the energy measured by an energy dispersive x-ray detector. In a preferred embodiment, the backscattered electrons and the x-rays are detected simultaneously, although they could be acquired sequentially or some data can be acquired simultaneously and other data acquired sequentially.

If it is determined in decision block 708 that not all points in the sample have been scanned, then the electron beam is moved to the next dwell point in step 710, and additional backscattered electrons and x-rays are collected at that dwell point. The scan continues until the desired portion of the sample surface, with x-rays and backscattered electrons being collected at each point.

After a scan is complete, the backscattered electron data are used to form an image of the sample in step 716. FIG. 8A shows a backscattered electron image 810 of the sample. In step 718, the backscattered electron image is analyzed to determine the outline of regions of the sample having similar characteristics. For example, FIG. 8A shows distinct regions 802A, 802B and 802C, which are observable on the backscattered electron image because each region is set apart on the bases of gray level and morphology. FIG. 8B shows symbols ("x", "o", and "+") representative of the x-ray quants collected in the regions 802A, 802B and 802C. X-ray quants collected as the beam scanned across the epoxy region between regions 802A, 802B and 802C are not shown. Thus, it is not required to collect sufficient quants at each dwell point to determine the composition of the region, because the quants from multiple dwell points are combined. Each symbol "x", "o", or "+" corresponds to a group of x-ray quants that comprise a spectrum but typically having insufficient quants for an accurate analysis of the composition at that dwell point.

In step 720, the x-rays collected while the beam was positioned at each of the dwell points within each of areas 802A, 802B, and 802C, are combined or clustered to form a single spectrum. The combined spectrum is analyzed in step 722. Decision block 724 determines whether or not sufficient x-rays have been accumulated to determine the material present in the sample. Because some peaks in the x-ray spectrum of different materials overlap, some materials require a more precise spectrum, that is, more detected x-rays, before it is possible to determine the material present with the desired degree of confidence. If it is determined in decision block 724 that sufficient x-rays have been collected, then the points in each of areas 802A, 802B, and 802C are assigned the composition determined in step 722 and the analysis is complete. FIG. 8C shows an extrapolated compositional map 814 of the sample, which was determined by assuming that regions having similar backscattered electron image characteristics are composed of the same material and combining the x-rays collected from each point in the region to determine the spectrum of the region. FIG. 8D shows an image that combines the information from the backscattered electron image and from the x-ray compositional image. In the combined image of FIG. 8D, a single symbol drawn in each region to signify the composition as determined by the combined spectrum of dwell points within each region. The combined data forms a third image, combining a first backscattered electron image and a second, single dwell point resolution x-ray image.

Combining the x-rays detected from dwell points, determined by the backscattered electron analysis to have common materials, greatly decreases the time required to acquire sufficient x-rays to determine the composition and provides more x-ray quants to produce a more reliable spectrum. Tens or hundreds of spectra can be added together from regions determined by the backscattered electron image to have the same phase or element. Combining the spectra can in some cases eliminate the need to rescan a region with the primary beam, thereby allowing the beam to scan different parts of the sample, while a previously scanned region is being processed to produce the spectral cube.

If decision block 724 determines that the x-rays collected are insufficient to determine the materials present, then the electron beam is directed to the sample again, and additional x-rays are collected. The electron beam can be scanned across the sample, scanned just in the region from which additional x-rays need to be collected, or the beam can be directed to one point in the center of the region to accumulate additional x-rays. It is desirable to collect x-rays from a flat region on the sample because features such as hills and valleys can distort the x-ray signal. The backscattered electron detector can provide topographical information, and the topographical information can be used to position the beam to a flat region to accumulate additional characteristic x-rays representative of the sample. As additional scans are taken to obtain additional x-rays, the backscattered electron image can also be refined with each additional scan. Reimaging the region reduces the signal to noise ratio. The boundaries of the regions on the backscattered electron image become more precise with each additional scan and additional regions of common composition may appear. This process is repeated until sufficient x-rays are detected to provide a compositional map with sufficient confidence, and then the process is completed.

While the embodiments above describe collecting and combining two-dimensional data, the invention is suitable for combining data from multiple modalities that produce three-dimensional information. As in the two-dimensional cases described above with respect to FIGS. 3-10, an image formed using a first modality can be combined with an image formed using a second modality, to produce a third image. The higher resolution or higher throughput of one modality can be used to improve the resolution or throughput of a second modality.

In one embodiment, three-dimensional electron tomography is used to form a three-dimensional image using transmitted electrons. Rather than determining a two-dimensional contour as shown in FIGS. 8A-8D, a three-dimensional contour is determined using a first modality. Compositional information is obtained by a second modality. For example, x-rays can be collected simultaneously as the series of electron images are collected to determine a three-dimensional compositional map of the sample. The sample progresses through a series of incremental tilts, typically between −70 degrees and positive 70 degrees, with one degree increments and a transmission electron image is obtained at each tilt. As the beam traverses the sample at multiple tilt angles of the sample, not only are the transmitted electrons detected to determine the three-dimensional contour, but x-rays from the sample can be simultaneously collected to determine the composition of the material. The beam scans the sample at a rate that is sufficient to obtain the contour information but is too fast to collect sufficient x-rays at each dwell point to determine the composition at that dwell point. By using the contour information from the electron image to group dwell points in three dimensions and combining information from the grouped points, sufficient compositional information is available for a reliable analysis. Because of the increased time to acquire a three-dimensional image, the advantages of the invention are even greater in three dimensions. The reduction in time required to form a three-dimensional compositional map provided by the invention is even greater than the time savings in two dimensions, because the number of dwell points is multiplied by the number of tilts in the tilt series.

In some embodiments, the contour or other information may be obtained by a non-scanning technique, such as transmission electron tomography using a parallel beam to form a bright field image, an energy loss image, or a diffraction image, while compositional information is obtained from a scan at a rate that is too fast to obtain enough information at each dwell point to characterize the material, but that obtains enough information at each dwell point so that when the dwell points are grouped based on the contour information, there is sufficient information for each group to determine its composition.

Matching a normalized x-ray spectrum provides qualitative information about which elements are present in a sample, but does not provide quantitative information about the relative quantity of these elements. The relative sizes of x-ray peaks depend not only on the number of atoms present, but also on the characteristics of the element and other factors. For example, there may be a large quantity of one element, but a relatively low probability of a particular electron transition, so the x-ray peak corresponding to that transition will be low.

Factors that affect the height of an x-ray peak include the atomic number of the element in the sample, the probability that an x-ray generated in the sample will be absorbed before reaching the sample surface, and the probability that an x-ray will react with an atom in the sample to fluoresce, that is, to emit a photon of a different energy. These factors are abbreviated as "ZAF factors," for atomic number ("Z"), absorption ("A"), and fluorescence ("F"). The angle between the sample surface and the detector, referred to as the "take-off angle," affects the absorption and fluorescence, so if a portion of a sample surface is tilted, the angle needs to be determined to adjust the ZAF factors to obtain a more precise quantitative analysis.

In accordance with another aspect of the invention, a backscattered electron detector is used to determine the take-off angle of portions of the sample, and then the take-off angle is used to modify the ZAF calculations to more accurately determine the relative quantity of materials in the sample. A backscattered electron detector can provide topographical information by detecting an asymmetrical pattern of backscattered electrons, for example by using an off-axis detector or using a segmented detector that can detect asymmetrically backscattered electrons. The topography information is preferably determined at each dwell point, so that the correction for a local take-off angle can be computed for each dwell point. In the prior art, a global tilt angle of the sample face was measured by any of various known methods, and a single global take-off angle was used for the entire sample. By determining a local take-off angle at each dwell point, a more accurate correction is possible. In other embodiments, a single take off angle may be used for groups of dwell points, rather than determining a take-off angle at each dwell point. For example, when a scan pattern such as the one shown in FIG. 4 is employed, a single takeoff angle may be determined for the group of dwell points in which x-rays are collected during a single x-ray detector integration period.

Figure 9:
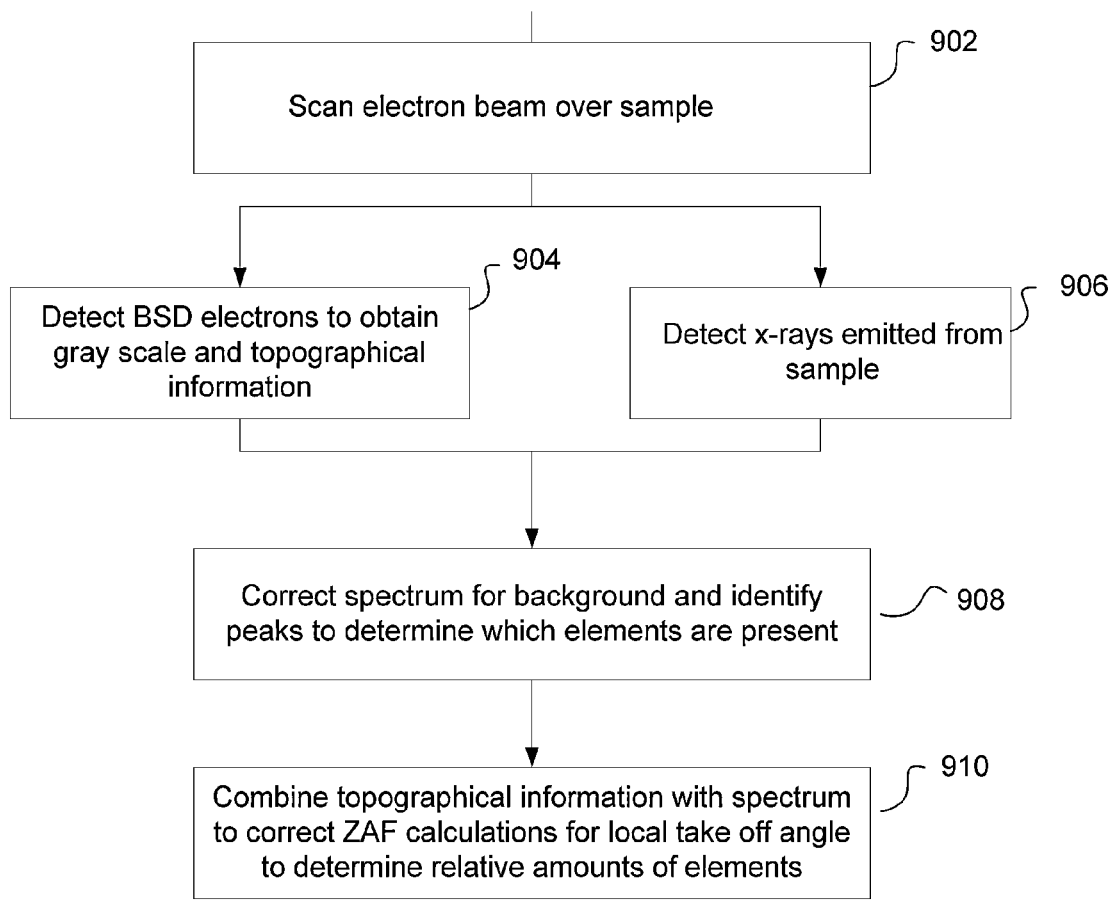
FIG. 9 shows the steps of an embodiment of the invention that uses local topographical information from backscattered electron detector information to improve quantification of compositional data.
Figure 10:
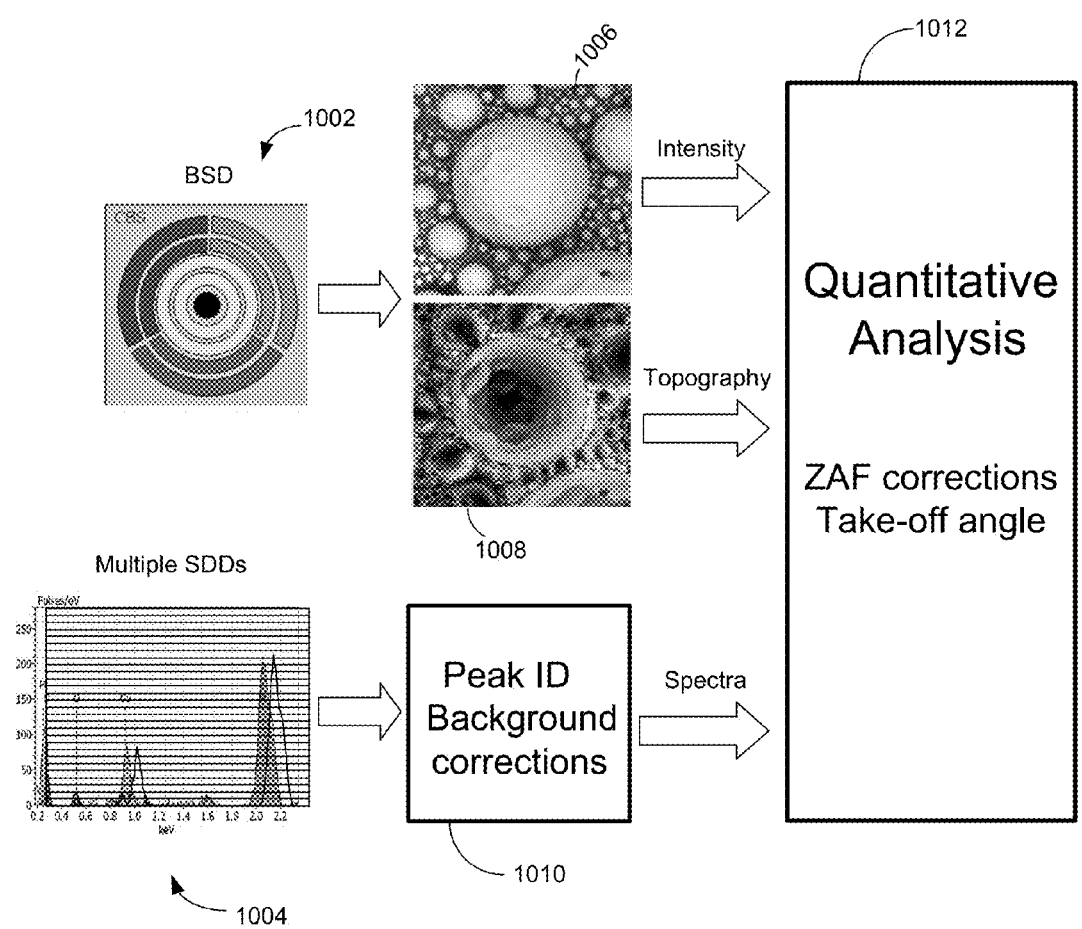
FIG. 10 illustrates the method of FIG. 9.

FIG. 9 shows a flow chart of the process of using the information from a backscattered electron detector in the analysis of information from the x-ray detector and FIG. 10 illustrates the steps in FIG. 9. In step 902, the electron beam is scanned over the sample. In step 904, backscattered electrons are detected using a backscattered electron detector that is segmented or using multiple off-axis detectors, so as to be able to detect electron that are backscattered asymmetrically about the primary electron beam axis. FIG. 10 shows a segmented backscattered electron detector 1002 that can detect when more backscattered electrons impinge on one side of the detector than on the other side. In step 906, x-rays are detected and the energies measured, using one or more x-rays detectors. X-ray spectrum 1004 (FIG. 10) is compiled preferably from x-ray energies measured by multiple silicon drift detectors. Image 1006 shows a feature on the sample using only gray scale information from backscattered electron detector 1002, that is, the backscattered electrons from all segments of the detectors are combined. Image 1008 shows the same features using topographical information from backscattered electron detector 1002, that is, the signals from the different sectors are processed to produce a signal proportional to the local tilt of the sample. Such signals are typically (A−B)/(A+B) type functions, that is, normalized difference-type functions. In step 908, background corrections are applied to the x-ray spectra and characteristic peaks are identified to determine the elements present. In step 910, information about the intensity and topography from the backscattered electron detector is combined with information about the spectral information from the x-ray detectors to perform a ZAF analysis with local take-off angle corrections to determine the relative amounts of elements found in the sample.

The techniques described herein are not limited to backscattered electron detectors and EDS—they can be used with any pair of detectors. Other analysis modalities that can be used to produce an image include energy loss spectroscopy (EELS), scanning transmission electron microscopy (STEM), wavelength dispersive spectroscopy (WDS), cathodeluminescence, stage current measurement, and secondary electron detection. An x-ray fluorescence system could also be used to generate x-rays from the sample.

The two types of modalities used typically include one high signal-to-noise ratio detector, such as a backscattered electron detector, a secondary electron detector, or an energy loss electron spectrometer, and a low signal-to-noise ratio detector, such as an x-ray detector or a cathodeluminescence detector. The information from the low signal-to-noise ratio detector is typically clustered by combining data from multiple points in a region determined to have similar composition by the high signal-to-noise ratio detector.

Figure 11:
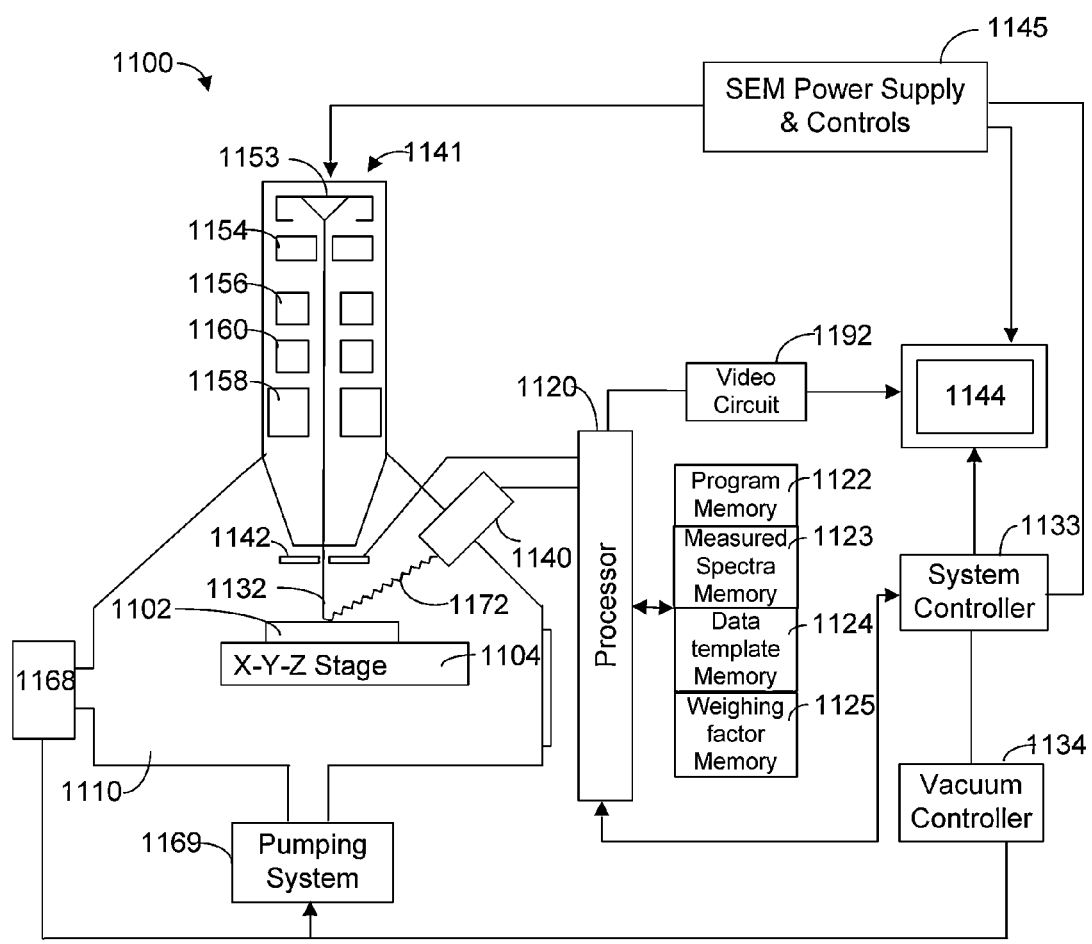
FIG. 11 shows typical hardware useful for implementing some embodiments of the invention.

FIG. 11 shows a scanning electron beam system 1100 with an x-ray detector 1140 suitable for practicing embodiments of the present invention. A scanning electron microscope 1141, along with power supply and control unit 1145, is provided with system 1100. An electron beam 1132 is emitted from a cathode 1153 by applying voltage between cathode 1153 and an anode 1154. Electron beam 1132 is focused to a fine spot by means of a condensing lens 1156 and an objective lens 1158. Electron beam 1132 is scanned two-dimensionally on the specimen by means of a deflection coil 1160. The deflector coils can deflect the beam along the x-axis and along the y-axis so that the beam can be scanned along a sample surface in a simple or complex pattern, such as a raster scan, serpentine scan, or a Hilbert scan. Deflectors can be magnetic or electrostatic. Operation of condensing lens 1156, objective lens 1158, and deflection coil 1160 is controlled by power supply and control unit 1145.

A system controller 1133 controls the operations of the various parts of scanning electron beam system 1100. The vacuum chamber 1110 is evacuated with ion pump 1168 and mechanical pumping system 1169 under the control of vacuum controller 1134.

Electron beam 1132 can be focused onto sample 1102, which is on a movable X-Y stage 1104 within lower vacuum chamber 1110. When the electrons in the electron beam strike sample 1102, the sample gives off x-rays whose energy correlates to the elements in the sample. X-rays 1172 having energy inherent to the elemental composition of the sample are produced in the vicinity of the electron beam incident region. Emitted x-rays are collected by x-ray detector 1140, preferably an energy dispersive detector of the silicon drift detector type, although other types of detectors could be employed, which generate a signal having an amplitude proportional to the energy of the detected x-ray. Backscattered electrons are detected by backscattered electron detector 1142, preferably a segmented silicon drift detector.

Output from detector 1140 is amplified and sorted by a processor 1120, which can comprise, for example, a microprocessor, a micro controller, a programmable gate array or any other digital or analog counts and sorts the total number of x-rays detected during a specified period of time, at a selected energy and energy resolution, and a channel width (energy range) of preferably between 10-20 eV per channel. Processor 1120 can comprise a computer processor, programmable gate array, or other digital or analog processing means; operator interface means (such as a keyboard or computer mouse); program memory 1122 for storing data and executable instructions; interface means for data input and output, executable software instructions embodied in executable computer program code; and display 1144 for displaying the results of a multivariate spectral analysis by way of video circuit 1192.

Processor 1120 can be a part of a standard laboratory personal computer, and is typically coupled to at least some form of computer-readable media. Computer-readable media, which include both volatile and nonvolatile media, removable and non-removable media, may be any available medium that can be accessed by processor 1120. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 1120.

Program memory 1122 can include computer storage media in the form of removable and/or non-removable, volatile and/or nonvolatile memory and can provide storage of computer-readable instructions, data structures, program modules and other data. Generally, the processor 1120 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 1122, such as the measured spectra memory portion 1123. Data template memory portion 1124 stores data templates, such as known spectra of elements or, in some embodiments, known diffraction patterns of materials. Weighing factor memory portion 1125 stores weighting factor for each of the data templates, the weighting factors combining with the data templates to produce a calculated spectrum approximating the measured spectrum. The weighting factors correlated to the abundance in the sample of the element corresponding to the data template. Processor 1120 uses the methods described above to minimize an error value which represents the difference between the measured pattern and the combination of the data templates and weighting factors.

It should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures described in this specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, sensors, and the like. Aspects of the present invention may be implemented in machine readable code stored as memory on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as aberration correctors or to a display monitor. In preferred embodiments of the present invention, the transformed data represents physical and tangible objects, including producing a particular visual depiction of the physical and tangible objects on a display.

Preferred embodiments of the present invention may make use of a particle beam apparatus, energy beam apparatus, or apparatus using a physical probe tip in order to image a sample. Such beams or physical probes used to image a sample inherently interact with the sample resulting in some degree of physical transformation. Further, throughout the present specification, discussions utilizing terms such as "calculating," "determining," "measuring," "generating," "detecting," "forming," "resetting," "reading," "subtracting," "detecting," "comparing," "acquiring," "mapping," "recording," "transforming," "changing," or the like, also refer to the action and processes of a computer system, a sensor, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out some embodiments of the present invention are commercially available, for example, from FEI Company, the assignee of the present application.

Further, whenever the terms "automatic," "automated," or similar terms are used herein, those terms will be understood to include manual initiation of the automatic or automated process or step. Whenever a scan or image is being processed automatically using computer processing, it should be understood that the raw image data can be processed without ever generating an actual viewable image. In the following discussion and in the claims, the terms "including" and "comprising" are used in an open-ended fashion, and thus should be interpreted to mean "including, but not limited to . . . ."

In accordance with one aspect of the invention, a method of determining properties of a sample comprises detecting using a first detector emissions of a first type from the sample in response to a beam scanned over an area of the sample; detecting using a second detector emissions of a second type from the sample in response to the beam scanned over the area of the sample, the second detector measuring spectral information; using emissions of the first type, dividing the scanned area of the sample into multiple regions, each region having a common characteristic; and combining emissions of the second type from multiple points in at least one of the regions determined using emissions of the first type to have a common characteristic to produce a combined spectrum of the material in the region.

In some embodiments of the invention, the first type of emissions comprises back scattered electrons or secondary electrons and in which the second type emissions include photons.

In some embodiments of the invention, detecting using a first detector emissions of a first type and detecting using a second detector emissions of a second type includes detecting emissions of the first and second type simultaneously as a beam is scanned over the area.

In some embodiments of the invention, detecting using a first detector emissions of a first type and detecting using a second detector emissions of a second type includes detecting emissions of the first and second type in subsequent scans of the beam.

In some embodiments of the invention, dividing the scanned area of the sample into multiple regions, each region having a common characteristic includes dividing the scanned area into multiple regions having similar contrast.

In some embodiments of the invention, the first detector integrates a signal over individual dwell points and in which the second detector integrates over multiple dwell points.

In some embodiments of the invention, the first detector and the second detector integrate signals during the scan pattern over different time periods.

In some embodiments of the invention, the emissions of a first type are acquired at a first rate and emissions of a second type are acquired at a second rate, the second rate being slower than the first rate.

In some embodiments of the invention, the first detector detects backscattered electrons to provide contrast information and in which the second detector detects x-rays to determine an x-ray spectrum to determine the composition of the sample.

In some embodiments of the invention, a local take-off angle determined by the first detector is used to correct information from the second detector information to determine relative quantitative compositional information about the sample.

In some embodiments of the invention, the second detector comprises an electron energy loss spectrometer, energy dispersive x-ray detector, or a wavelength dispersive x-ray detector, stage current detector, or secondary electron detector.

In some embodiments of the invention, the first detector determines a region of the sample having a common composition at a first resolution; the second detector determines the composition of the region at a second resolution, lower than the first resolution; and the system determines the composition of the region determined by the first detector using the information by the second detector.

In some embodiments of the invention, the first detector detects emissions from a first interaction volume smaller than an interaction volume of the second detector and the embodiment further comprising determining properties of regions of the sample having a boundary, the position of the boundary being determined by the first detector and the properties of the region on either side of the boundary being determined by the second detector.

In some embodiments of the invention, if the second detector has not detected sufficient emissions for analysis, the beam scans the sample again.

In accordance with another aspect of the invention, a beam system comprises a source of a primary beam to be directed to a sample; a first detector for detecting first emissions from the sample caused by the impingement of the primary beam; a second detector for detecting second emissions from the sample caused by the impingement of the primary beam; and a program memory including computer instructions for performing the method of any of the above embodiments.

To the extent that any term is not specially defined in this specification, the intent is that the term is to be given its plain and ordinary meaning. The accompanying drawings are intended to aid in understanding the present invention and, unless otherwise indicated, are not drawn to scale. Although the present invention and its advantages have been described in detail, it should be understood that various changes, substitutions and alterations can be made herein without departing from the invention as defined by the appended claims. Moreover, the present application is not intended to be limited to the particular embodiments of the process, machine, manufacture, composition of matter, means, methods and steps described in the specification.

As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include such processes, machines, manufacture, compositions of matter, means, methods, or steps.

We claim as follows:

1. A method of determining properties of a sample, comprising:
    detecting using a first detector emissions of a first type from the sample in response to a beam scanned over an area of the sample;
    detecting using a second detector emissions of a second type from the sample in response to the beam scanned over the area of the sample, the second detector measuring spectral information;
    using emissions of the first type, dividing the scanned area of the sample into multiple regions, each region having a common characteristic;
    characterized by:
    combining emissions of the second type from multiple points at different position along the scan in at least one of the regions determined using emissions of the first type to have a common characteristic to produce a combined spectrum of the material in the region.

2. The method of claim 1 in which the first type of emissions comprises back scattered electrons or secondary electrons and in which the second type emissions include photons.

3. The method of claim 1 in which detecting using a first detector emissions of a first type and detecting using a second detector emissions of a second type includes detecting emissions of the first and second type simultaneously as a beam is scanned over the area.

4. The method of claim 3, further comprising:
progressing the sample through a series of incremental tilts;
obtaining an image at each tilt, by scanning the sample at a rate that is sufficient to obtain contour information from the first detector but is too fast to collect sufficient spectral information at each dwell point to determine the composition at that dwell point; and
using the contour information to group dwell points in three dimensions and combining compositional information from the grouped points, from which sufficient compositional information is obtained.

5. The method of claim 4, wherein the contour or other information is obtained by a non-scanning technique.

6. The method of claim 5, in which the non-scanning technique includes transmission electron tomography using a parallel beam to form a bright field image, an energy loss image, or a diffraction image.

7. The method of claim 1 in which detecting using a first detector emissions of a first type and detecting using a second detector emissions of a second type includes detecting emissions of the first and second type in subsequent scans of the beam.

8. The method of claim 1 in which the first detector and the second detector integrate signals during the scan pattern over different time periods.

9. The method of claim 1 in which the emissions of a first type are acquired at a first rate and emissions of a second type are acquired at a second rate, the second rate being slower than the first rate.

10. The method of claim 1 in which the first detector detects backscattered electrons to provide contrast information and in which the second detector detects x-rays to determine an x-ray spectrum to determine the composition of the sample.

11. The method of claim 10 in which a local take-off angle determined by the first detector is used to correct information from the second detector information to determine relative quantitative compositional information about the sample.

12. The method of claim 1 in which the second detector comprises an electron energy loss spectrometer, energy dispersive x-ray detector, or a wavelength dispersive x-ray detector, stage current detector, or secondary electron detector.

13. The method of claim 1 in which:
detecting using a first detector includes determining a region of the sample having a common composition at a first resolution;
detecting using a second detector includes determining the composition of the region at a second resolution, lower than the first resolution; and
determining the composition of the region determined by the first detector using the information from the second detector.

14. The method of claim 1 in which:
detecting using a first detector includes detecting emissions from a first interaction volume smaller than an interaction volume of the second detector:
further comprising determining properties of regions of the sample having a boundary, the position of the boundary being determined by the first detector and the properties of the region on either side of the boundary being determined by the second detector.

15. The method of claim 14, in which:
detecting using a first detector includes detecting emissions from a first interaction volume having a first resolution;
detecting using a second detector includes detecting emissions from a second interaction volume having a second resolution, lower than the first resolution; and
incorporating an image detected from the higher-resolution first detector into an image detected from the lower-resolution second detector to locate the change in property measured by the second detector at a higher resolution.

16. The method of claim 1 in which, if the second detector has not detected sufficient emissions for analysis, the beam scans the sample again.

17. A beam system, comprising:
a source of a primary beam to be directed to a sample;
a first detector for detecting first emissions from the sample caused by the impingement of the primary beam;
a second detector for detecting second emissions form the sample caused by the impingement of the primary beam;
a system controller including a program memory storing machine readable instructions for performing the method of claim 1.

18. A beam system of claim 17, in which the program memory stores instructions for:
detecting backscattered electrons from the first detector to provide contrast information;
detecting X-rays from the second detector to determine an X-ray spectrum to determine the composition of the sample;
determining from the detector a local take-off angle; and
using the local take-off angle to correct information from the second detector to determine relative quantitative compositional information about the sample.

19. A method of determining properties of a sample, comprising:
detecting using a first detector emissions of a first type from the sample in response to a beam scanned over an area of the sample;
detecting using a second detector emissions of a second type from the sample in response to the beam scanned over the area of the sample, the second detector measuring spectral information;
using emissions of the first type, dividing the scanned area of the sample into multiple regions, each region having a common characteristic includes dividing the scanned area into multiple regions having similar contrast;
characterized by:
combining emissions of the second type from multiple points in at least one of the regions determined using emissions of the first type to have a common characteristic to produce a combined spectrum of the material in the region.

20. A method of determining properties of a sample, comprising:
detecting using a first detector emissions of a first type from the sample in response to a beam scanned over the area of the sample, the first detector integrating a signal over individual dwell points;
detecting using a second detector emissions of a second type from the sample in response to the beam scanned over the area of the sample, the second detector measuring spectral information and integrating over multiple dwell points;

using emissions of the first type, dividing the scanned area of the sample into multiple regions, each region having a common characteristic;

characterized by:

combining emissions of the second type from multiple points at different position along the scan in at least one of the regions determined using emissions of the first type to have a common characteristic to produce a combined spectrum of the material in the region.

* * * * *